United States Patent [19]

Ludwig et al.

[11] Patent Number: 5,326,777
[45] Date of Patent: Jul. 5, 1994

[54] MICROBICIDAL COMBINATIONS OF ACTIVE COMPOUNDS

[75] Inventors: Georg-Wilhelm Ludwig, Krefeld; Otto Exner, Ratingen; Hans-Georg Schmitt, Krefeld; Karl-Heinz Büchel, Burscheid; Graham Holmwood, Wuppertal, all of Fed. Rep. of Germany

[73] Assignee: Bayer Aktiengesellschaft, Leverkusen, Fed. Rep. of Germany

[21] Appl. No.: 907,496

[22] Filed: Jul. 1, 1992

[30] Foreign Application Priority Data

Jul. 11, 1991 [DE] Fed. Rep. of Germany ....... 4122868

[51] Int. Cl.$^5$ ..................... A01N 43/52; A01N 43/64
[52] U.S. Cl. ..................................... 514/383; 514/388
[58] Field of Search ............................... 514/383, 388

[56] References Cited

FOREIGN PATENT DOCUMENTS 0052424  5/1982  European Pat. Off. .
2059773  9/1980  United Kingdom .

OTHER PUBLICATIONS

Chemical Abstracts, vol. 115, No. 1, Jul. 8, 1991, 115:3160f.

*Primary Examiner*—Allen J. Robinson
*Attorney, Agent, or Firm*—Sprung Horn Kramer & Woods

[57] ABSTRACT

Microbicidal synergistic combinations of active compounds composed of known azol and benzimidazole derivatives are described, as is their use in the protection of materials.

1 Claim, No Drawings

MICROBICIDAL COMBINATIONS OF ACTIVE COMPOUNDS

The present invention relates to new microbicidal, synergistic combinations of active compounds comprising known azol and benzimidazole derivatives.

Imidazol fungicides and triazole fungicides, such as for example α-[2-(4-chlorophenyl)-ehtyl)-α-(1,1-dimethylethyl)1-H-1,2,4-triazole-1-ethanol (tebuconazole) and 1-[[2-(2,4-dichlorophenyl)-4-n-propyl-1,3-dioxolan-2-yl]methyl-]-1H-1,2,4-triazole (propiconazole) and their use for the protection of plants and seed are known (compare for example EP-A-0,040,345, EP-A 0,052,424). It is further known that these compounds can also be used to protect industrial materials from microbes (compare DE-OS (German Published Specification) 3,905,378, DE-OS (German Published Specification) 3,621,494).

It is further known that benzimidazole derivatives such as methyl benzimidazolylcarbamate (BCM, carbendazim), methyl 1-(butylcarbamoyl)-2-benzimidazolecarbamate (benomyl), 2-(2'-furyl)-1H-benzimidazole (fuberidazole) and 2-(4'-thiazolyl)-benzimidazole possess a fungicidal activity (Farm Chemicals Handbook). These can also be used in the protection of materials.

It is a disadvantage of these two classes of compound that their level of activity and spectrum of activity is not always sufficient to protect industrial materials, in particular plastics, as for example discoloration of the plastics originates from the high application rates required.

It has now been found that combinations of active compounds comprising at least one azol derivative, preferably 1-(4-chlorophenoxy)-3,3-dimethyl-1-(1H-1,2,4-triazol-1-yl)2-butanones, (triadimefon), β-(4-chlorophenoxy)-α-(1,1-dimethyl-ethyl)-1H-1,2,4-triazole-1-ethanol, (triadimenol), ±-α-[2-(4-chlorophenyl)-ethyl]-α-(1,1-dimethylethyl)-1H-1,2,4-triazole-1-ethanol, (tebuconazole)-(RS)-2(2,4-dichlorophenyl)-1-(1H-1,2,4-triazole-2-yl)-ethan-2-ol, (hexaconazole)-1-(N-propyl-N-(2-(2,4,6-(trichlorophenoxy)-ethyl)-carbamoyl)-imidazole, (prochloraz), their metal salts or acid addition compounds and in the cases where the compound has an asymmetric carbon atom, also the isomers and mixtures of isomers of the widest composition;

very particularly preferably ±α-[2-(4-chlorophenyl)ethyl]-α-(1,1-dimethylethyl)-1H-1,2,4-triazole-1-ethanol (tebuconazole), having at least one benzimidazole derivative of the formula (I)

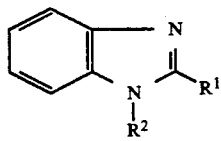

in which
R¹ represents carbamate groups, optionally further substituted furyl rings or thiazolyl rings and
R² represents H or carbamate groups,
have a particularly high microbicidal activity.

Benzimidazole derivatives which can be mentioned are preferably:

methyl benzimidazolylcarbamate (BCM), methyl 1-(butylcarbamoyl)-2-benzimidazolecarbamate (benomyl), 2-(2'-furyl)-1H-benzimidazole and 2-(4'-thiazolyl)-benzimidazole.

Particular preference is given to methyl benzimidazolylcarbamate (BCM).

Very particular preference is given to the combination of tebuconazole and BCM.

Surprisingly, the microbicidal, in particular the fungicidal, activity of the combinations of active compounds according to the invention is substantially higher than the sum of the activities of the individual active compounds. A true synergistic effect is therefore present. The combinations of active compounds provide a valuable extension of the technique, inasmuch as the above-described risk of discoloration is markedly reduced.

The azol derivatives and the benzimidazole derivatives can not only exist in the form of their free bases but also preferably in the form of their metal salt complexes or as acid addition salts. The metal salts in question can be preferably salts of metals of main groups II to IV and of subgroups I and II and also IV to VII of the Periodic Table, where copper, zinc, manganese, magnesium, tin, iron, calcium, aluminium, lead, chromium, cobalt and nickel may be mentioned as examples.

Anions of the salts which can be used are preferably those derived from the following acids: hydrohalic acids, such as for example hydrochloric acid and hydrobromic acid, and in addition phosphoric acid, nitric acid and sulphuric acid.

The metal salt complexes can be obtained in a simple manner according to conventional processes, for example by dissolution of the metal salt in alcohol, for example ethanol, and addition to the azol derivative or benzimidazol derivative. Metal salt complexes can be isolated in a known manner, for example by filtration, and, if required, be purified by recrystallisation.

To prepare the acid addition salts, the following acids can preferably be used: the hydrohalic acids, such as for example hydrochloric acid and hydrobromic acid, in particular hydrochloric acid, and in addition phosphoric acid, nitric acid, sulphuric acid, mono- and bifunctional carboxylic acids and hydroxycarboxylic acids, such as for example acetic acid, propionic acid, butyric acid, mandelic acid, oxalic acid, succinic acid, 2-hydroxyethane-dicarboxylic acid, maleic acid, fumaric acid, tartaric acid, citric acid, salicylic acid, sorbic acid, lactic acid and sulphonic acids, such as for example p-toluenesulphonic acid, 1,5-naphthalenedisulphonic acid, alkanesulphonic acids and optionally substituted benzoic acids.

The acid addition salts of the compounds can be obtained in a simple manner by conventional salt formation methods, for example by dissolving a compound in a suitable inert solvent and adding the acid, for example hydrochloric acid, and can be isolated in a known manner, for example by filtration, and, if required, can be purified by washing with an inert organic solvent.

The weight ratios of the active compounds in the combinations of active compounds can be varied within relatively large ranges. The mixtures contain the azol component in amounts of 1 to 99% by weight, the remainder up to 100% is the benzimidazole component.

The mixing ratio of azol component to benzimidazole component is preferably 1:9 to 9:1, particularly preferably 2:8 to 8:2 parts by weight.

The combinations of active compounds according to the invention have a high activity against microorganisms. The combinations of active compounds according to the invention are used in the protection of materials to protect industrial materials; they are principally effective against moulds, plastic-discoloring and plastic-destroying fungi and bacteria. As examples, but without restriction thereto, the following genera of microorganisms may be mentioned:

Alternaria such as *Alternaria tenuis*, Aspergillus such as *Aspergillus niger* and *Aspergillus terreus*, Aureobasidium such as *Aureobasidium pullulans*, Chaetomium such as *Chaetomium globosum*, Cladosporium such as *Cladosporium herbarum*, Coniophora such as *Coniophora puteana*, Gliocladium such as *Gliocladium virens*, Lentinus such as *Lentinus tigrinus*, Paecilomyces such as *Paecilomyces varioti*, Penicillium such as *Penicillium brevicaule*, *Penicillium glaucum* and *Penicillium pinophilum*, Polyporus such as *Polyporus versicolor*, Sclerophoma such as *Sclerophoma pityophila*, Streptoverticillium such as *Streptoverticillium reticulum*, Trichoderma such as *Trichoderma viride*, Trichophyton such as *Trichophyton mentagrophytes*;

Escherichia such as *Escherichia coli*, Pseudomonas such as *Pseudomonas aerugionosa*, Staphylococcus such as *Staphylococcus aureus*;

Candida such as *Candida albicans*.

The amount of the combinations of active compounds used is dependent on the species and incidence of the microorganism, the microbial count and the medium. The optimal application rate can be determined by the use of test series in each case. However, generally it is sufficient to use 0.001 to 5% by weight, preferably 0.05 to 2% by weight of the active compound mixtures, relative to the material to be protected.

The new combinations of active compounds can be used as such, in the form of concentrates or in the form of generally conventional formulations such as powders, granules, solutions, suspensions, emulsions or pastes.

The formulations mentioned can be prepared by a method in itself known, for example by mixing the active compounds with a solvent or diluent and, if required, further processing aids, such as for example emulsifiers and dispersants.

The solvents or diluents used are preferably all solvents or diluents used for the processing of plastics.

Plastics is here taken to mean a multiplicity of different polymeric materials, such as thermoplastic polymers, thermosetting resins, elastomers and naturally occurring polymers.

Thermoplastic polymers include polyolefins such as for example polyethylene, polypropylene and polybutylene, (modified) polyvinyl chloride, polystyrene and styrene copolymers, acrylostyrene and styrene copolymers, acrylic resins, fluoropolymers, polyamides, polycarbonates, polyesters such as for example polyethyleneterephthalate, polyethylenenaphthalate, linear epoxy resins and blends thereof.

Thermosetting resins include formaldehyde resins such as for example phenol/formaldehyde resins, unsaturated polyester resins, silicone resins, polyimides, epoxy resins and crosslinked polyurethanes such as PUR foams, PUR casting resins, PUR paints and PUR adhesives. Elastomers are rubbers such as for example natural rubbers, isoprene rubber, styrene/butadiene rubber, butadiene rubber and chloroprene rubber and polyurethane elastomers.

The incorporation of the combinations of active compounds is carried out by generally conventional methods, for example by blending the combination of active compounds or the individual active components with the starting materials, solvents and/or additives required for the polymerisation.

Furthermore, the incorporation advantageously depends on the type and method of production of each plastic material. For example, incorporation into PVC systems and into polyurethane systems may be mentioned here, without restrictive effect.

In the case of PVC systems, the incorporation is advantageously carried out by direct addition of the active compound combination as such during compounding. Alternatively, the active component or the combination of active compounds can be used as a "master batch" in solvents tolerated by the system or in one of the plasticisers used or in other suitable additives.

The solvents used can be for example: aliphatic and araliphatic alcohols such as for example isodecyl alcohol, 2-ethylhexanol, 2-ethyl-1,3-hexanediol, benzyl alcohol, phenethyl alcohol, and phenoxyethanol.

Examples of plasticisers are phthalates, such as for example di-(2-ethylhexyl) phthalate, dicyclohexyl phthalate, diisobutyl phthalate, diisodecyl phthalate, mixed n-alkyl phthalates, butyl benzyl phthalate, di-n-octyl phthalate, di-n-decyl phthlate, phosphates such as for example tricresyl phosphate, diphenyl cresyl phosphate, alkyl-aryl phosphates, carboxylates such as dioctyl adipate, dipropylene glycol dibenzoate, dioctyl azelate, epoxidised soya bean oil.

In the case of polyurethane systems, the incorporation is advantageously carried out prior to polymerisation by direct addition of the combination of active compounds to one component. Alternatively, the components of the polyurethane system such as polyols, isocyanate components or crosslinker systems can be supplied with the combination of active compounds. In principle, the individual components of the active compound mixture can also be introduced into different component of the polyurethane system.

To the combinations of active compounds according to the invention, preparations which can be prepared therefrom, concentrates or formulations in general, can, if required, be added further fungicides, insecticides or other active compounds to increase the activity spectrum or to achieve particular effects, such as for example additional protection from insects. Particularly expedient components are, for example, the following compounds;

The activity and the activity spectrum of the active compound combination according to the invention and the agents, concentrates or diverse formulations which can be prepared therefrom can be increased if other antimicrobially active compounds, fungicides, bactericides, herbicides, insecticides or other active compounds for broadening the activity spectrum of for obtaining special effects, such as for example additional protection against insects, are added as required. These mixtures can have a broader spectrum of activity than the compounds according to the invention. In many cases synergistic effects are thereby obtained, i.e. the activity of the mixture is greater than the activity of the individual components. Particularly effective components of the mixtures are, for example, the following compounds:

Sulphenamides such as dichlofluanid (euparen), tolylfluanid (methyleuparen), folpet and fluorofolpet; thiocyanates such as thiocyanatomethylthiobenzothiazole (TCMTB) and methylenebisthiocyanate (MBT); and quaternary ammonium compounds such as benzyldimethyltetradecylammonium chloride, benzyl-dimethyldodecyl-ammonium chloride and didecyl-dimethylammonium chloride; morpholine derivatives such as $C_{11}$–$C_{14}$ 4-alkyl-2,6-dimethylmorpholine homologues (tridemorph), falimorph, ($\pm$)-cis-4-[3-tert.-butylphenyl]-2-methylpropyl]-2,6-dimethylmorpholine (fenpropimorph) and carbamorph; phenols such as o-phenylphenol, tribromophenol, tetrachlorophenol, pentachlorophenol, 3-methyl-4-chlorophenol, dichlorophene, chlorophene or salts thereof; iodopropargyl derivatives such as iodopropargyl-butylcarbamate (IPBC), -chlorophenylformal, -phenylcarbamate, -hexylcarbamate, -cyclohexylcarbamate, and iodopropargyloxyethyl iodine derivatives such as diiodomethyl-p-arylsulphones, such as diiodomethyl-p-tolylsulphone; bromine derivatives such as bronopol; isothiazolinones such as N-methylisothiazolin-3-one, 5-chloro-N-methylisothiazolin-3-one, 4,5-dichloro-N-octylisothiazolin-3-one, N-octylisothiazolin-3-one (octhilinone); benzisothiazolinone, cyclopenteneisothiazolinone; pyridines such as 1-hydroxy-2-pyridinethione (and its Na, Fe, Ma and Zn salts), tetrachloro-4-methylsulphonylpyridine; metallic soaps such as tin, copper and zinc naphthenate, octoate, 2-ethylhexanoate, oleate, phosphate, benzoate, and oxides such as TBTO, $Cu_2O$, CuO, ZnO; organic tin compounds such as tributyltin naphthenate and tributyltin oxide; dialkyl dithiocarbamates such as Na and Zn salts of dialkyl dithiocarbamates, tetramethyldiuram disulphide (TMTD); nitriles such as 2,4,5,6-tetrachloroisophthalonitrile (chlorothalonil) etc, microbicides containing activated halogen groups such as Cl-Ac, MCA, tectamer, bronopol, bromidox; benzthiazoles such as 2-mercaptobenzothiazole; see above: dazomet, quzinolines such as 8-hydroxyquinoline or its halogenated derivatives such as haloquinal, broxyquinoline or cliogrinal; formaldehyde-releasing compounds such as benzyl alcohol mono(poly)hemiformal, oxazolidine, hexahydro-S-triazine, N-methylol chloroacetamide; tris-N-(cyclohexyldiazeniumdioxy)-aluminium, N-(cyclohexyldiazeniumdioxy)-tributyltin or K salts, bis-(N-cyclohexyl)diazinium (-dioxy-copper or aluminium); and sulphur or sulphur products such as for example inorganic polysulphides, sulphur or azithiram.

Insecticides which are preferably used are: phosphoric acid esters such as azinphos-ethyl, azinphos-methyl, 1-(4-chlorophenyl)-4-(O-ethyl, S-propyl)-phosphoryloxypyrazole (TIA-230), chlorpyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulfoprofos, triazophos and trichlorphon; carbamates such as aldicarb, bendiocarb, BPMC (2-(1-methylpropyl)phenylmethyl carbamate), butocarboxim, butoxicarboxim, darbaryl, carbofuran, carbosulfan, cloethocarb, isoprocarb, methomyl, oxamyl, pirimicarb, promecarb, propoxur and thiodicarb; pyrethroids such as allethrin, alphamethrin, bioresmethrin, byfenthrin (FMC 54 800), cycloprothrin, cyfluthrin, decamethrin, cyhalothrin, cypermethrin, deltamethrin, alpha-cyano-3-phenyl-2-methylbenzyl-2,2-dimethyl-3-(2-chloro-2trifluoromethylvinyl)cyclopropane carboxylate, fenpropathrin, fenfluthrin, fenvalerate, flucythrinate, flumethrin, fluvalinate, permethrin and resmethrin; nitroimino and nitromethylenes such as 1-[(6-chloro-3-pyridinyl)-methyl]-4,5-dihydro-N-nitro-1H-imidazol-2-amine (imidacloprid).

Other suitable active compounds are algicides, molluscides and active compounds against sea animals which attach themselves, for example, to the paintwork on the undersides of ships.

The microbicidal preparations or concentrates used to protect industrial materials contain the combinations of active compounds according to the invention at a concentration of 0.01 to 95% by weight, in particular 0.01 to 60% by weight, in addition, if required, 0.001 to 10% by weight of a suitable further fungicide, insecticide or further active compound as mentioned above.

The combinations of active compounds according to the invention allow the hitherto available microbicidal preparations to be replaced, in an advantageous manner, by more effective and more environmentally acceptable ones. They show good stability and have, in an advantageous manner, a broad spectrum of activity.

The following examples illustrate the invention without restricting it thereto. Parts and percentages denote parts by weight and percentages by weight.

EXAMPLE A

1. Synergistic fungicide mixture of tebuconazole and methyl benzimidazolylcarbamate (BCM)

80 parts by weight of tebuconazole and 20 parts by weight of BCM are intimately mixed as solids or are ground together in a suitable mill. The synergistic fungicide mixture results as a white powder.

Mixtures having the other mixing ratios of the components can be prepared analogously.

2. Synergistic activity of the active compounds according to the invention against plastic-destroying fungi.

The synergistic activity of the active compound mixtures according to the invention can result from the comparison of the activity of the pure substances with that of the mixture.

PREPARATION OF THE TEST MATERIAL

1% of the combination of active compounds is stirred at room temperature into the polyester/polyol used for the preparation of polyurethane. After addition of the crosslinker, the mixture is reacted with the isocyanate component. A 1-cm-thick layer of polyurethane foam results.

For microbiological analysis, the layer is split to 2 mm thickness and a microbiological test is carried out according to Swiss Testing Standard SNV 195921.

For this purpose, round testing bodies are stamped out ($\phi$3 cm). After sterilisation, these are deposited on an agar comprising a lower, uncontaminated, and an upper, contaminated agar layer. The agar is incubated at 26° C. for 4 weeks.

EVALUATION

The extent of overgrowth of the testing bodies by the microorganisms and also the size of the growth-free zone surrounding the testing bodies (inhibition zone) are a measure of the microbiological activity (see following evaluation scheme).

The result for the synergistic fungicide mixture of 80% tebuconazole+20% BCM, see Table 1.

| Evaluation scheme | | | |
|---|---|---|---|
| Inhibition zone in mm | Growth[1] | Description | Evaluation |
| n to 1 | none | inhibition zone greater than 1 mm, no more growth | good action, pronounced inhibition zone[2] |
| 1 to 0 | none | inhibition zone up to 1 mm, no more growth | good action[2] |
| 0 | none | no inhibition zone, no growth | good action[3] |
| 0 | poor | no inhibition zone, almost no growth | unsatisfactory limit of action |
| 0 | medium | no inhibition zone, growth reduced to about half that of the control | unsatisfactory |
| 0 | full | no inhibition zone, growth not, or only slightly reduced in comparison to control | unsatisfactory |

[1] Growth means the bacterial or mould colonisation in the nutrient medium, in the case of bacteria under, or in the case of moulds on or under, the testing body.
[2] Only restricted importance can be attached to the size of the inhibition zone. A large inhibition zone can indicate certain reserves of active compound or a poor fixation of a preparation on the substrate.
[3] With the lack of growth, the activity is described as good, despite the lack of inhibition zone, as the formation of an inhibition zone is possibly prevented by a low diffusibility of the active substance.

TABLE 1

Example A
Agar diffusion test according to Swiss Testing Standard SNV 195 921 PU testing body containing as microbicide

| Microorganisms/ concentration in the polyester/ polyol | 0 sample | Active Compound A 1% | Active Mixture B 1% | Active Compound C 0.2% |
|---|---|---|---|---|
| Chaetomium globosum | 0 | 0 | 15 | 10 |
| Aspergillus niger | 0 | 0 | 5–8 | 4–5 |
| Aspergillus terreus | 0 | 0 | 9 | 5–7 |
| Trichoderma viride | 0 | 0 | 0–1 | 0–1 |
| Cladosporium herbarum | 0 | 0 | 18 | 15–17 |
| Penicillium brevicaule | 0 | 0 | 6 | 4–5 |

Active compound A = tebuconazole
Active Mixture B = 80 parts of tebuconazole/20 parts of methyl benzimidazolylcarbamate
Active compound C = methyl benzimidazolcarbamate

TABLE 2

Example B
Agar diffusion test according to Swiss Testing Standard SNV 195 921 PU testing body containing as microbicide

| Microorganisms/ concentration in the polyester/ polyol | 0 sample | Active Compound A 1% | Active Mixture B 1% | Active Compound C 0.2% |
|---|---|---|---|---|
| Chaetomium globosum | 0 | 0 | 12 | 10–12 |
| Aspergillus niger | 0 | 0 | 1–3 | 0–1 |
| Cladosporium herbarum | 0 | 0 | 11 | 8–11 |
| Penicillium brevicaule | 0 | 0 | 0–1 | 0 |
| Trichophyton mentagrophytes | 0 | 0 | 12 | 8–10 |

Active compound A = tebuconazole
Active Mixture B = 80 parts of tebuconazole/20 parts of 2(4'-thiazolyl)-benzimidazole
Active compound C = 2(4'-thiazolyl)-benzimidazole

EXAMPLE B

1. Synergistic fungicide mixture of tebuconazole and 2-(4'-thiazolyl)-benzimidazole (TBZ)

80 parts by weight of tebuconazole and 20 parts by weight of TBZ are intimately mixed as solid or are ground together in a suitable mill. The synergistic fungicide mixture results as a white powder.

Mixtures having the other mixing ratios of the component can be prepared analogously.

2. Synergistic activity of the active compound according to the invention against plastic-destroying fungi.

The synergistic activity of the active compound mixtures according to the invention can result from the comparison of the activity of the pure active compounds with that of the mixture.

Preparation of the testing material and carrying out of the test proceed analogously to Example A.

The result for the synergistic fungicide mixture of 80% tebuconazole and 20% TBZ is recorded in Table 2.

EXAMPLE C

1. Synergistic fungicide mixture of tebuconazole and 2-(2'-furyl)-benzimidazole (FBZ)

80 parts by weight of tebuconazole and 20 parts by weight of FBZ are intimately mixed as solid or are ground together in a suitable mill. The synergistic fungicide mixture results as a white powder.

Mixtures having the other mixing ratios of the component can be prepared analogously.

2. Synergistic activity of the active compounds according to the invention against plastic-destroying fungi.

The synergistic activity of the active compound mixtures according to the invention can result from the comparison of the activity of the pure active compounds with that of the mixture.

Preparation of the testing material and carrying out of the test proceed analogously to Example A.

The result for the synergistic fungicide mixture of 80% tebuconazole and 20% FBZ is recorded in Table 3.

TABLE 3

Example C

Agar diffusion test according to Swiss Testing Standard SNV 195 921 PU testing body containing as microbicide

| Microorganisms/ concentration in the polyester/ polyol | 0 sample | Active Compound A 1% | Active Mixture B 1% | Active Compound C 0.2% |
| --- | --- | --- | --- | --- |
| Chaetomium globosum | 0 | 0 | 4–5 | 3 |
| Cladosporium herbarum | 0 | 0 | 3–8 | 1–2 |
| Trichophyton mentagrophytes | 0 | 0 | 0–3 | 0 |

Active compound A = tebuconazole
Active Mixture B = 80 parts of tebuconazole/20 parts of 2(2'-furyl)-benzimidazole
Active compound C = 2(2'-furyl)-benzimidazole

We claim:

1. A method of protecting plastics from fungi, said method comprising applying to said plastics a fungicidally effective amount of a synergistic mixture of tebuconazole or a salt thereof and carbendazim in a synergistic weight ratio of tebuconazole to carbendazim of from 1:9 to 9:1.

* * * * *